United States Patent
Shibuya et al.

(10) Patent No.: US 7,183,265 B2
(45) Date of Patent: *Feb. 27, 2007

(54) POWDERY PRODUCT COMPRISING CRYSTALLINE β-MALTOSE MONOHYDRATE, ITS PREPARATION, AND USES

(75) Inventors: Takashi Shibuya, Okayama (JP); Toshiyuki Sugimoto, Okayama (JP); Toshio Miyake, Okayama (JP)

(73) Assignee: Kabushiki Kaisha Hayashibara Seibutsu Kagaku Kenkyujo, Okayama (JP)

( * ) Notice: Subject to any disclaimer, the term of this patent is extended or adjusted under 35 U.S.C. 154(b) by 23 days.

This patent is subject to a terminal disclaimer.

(21) Appl. No.: 11/133,416

(22) Filed: May 20, 2005

(65) Prior Publication Data

US 2005/0215451 A1  Sep. 29, 2005

Related U.S. Application Data

(63) Continuation of application No. 10/468,795, filed as application No. PCT/JP02/08410 on Aug. 21, 2002, now Pat. No. 6,897,202.

(30) Foreign Application Priority Data

Aug. 22, 2001 (JP) ............................. 2001/252157

(51) Int. Cl.
 *A61K 31/715* (2006.01)
 *A61K 31/7016* (2006.01)
 *A61K 31/702* (2006.01)
 *C07H 3/04* (2006.01)
 *C07H 3/06* (2006.01)

(52) U.S. Cl. ..................... 514/53; 514/54; 536/123.13; 536/4.1; 536/124; 536/123.1

(58) Field of Classification Search ................. 514/53, 514/54; 536/123.13, 4.1, 124, 123.1
See application file for complete search history.

(56) References Cited

U.S. PATENT DOCUMENTS

| 3,677,896 | A | | 7/1972 | Kurimoto et al. |
| 3,804,715 | A | | 4/1974 | Sugimoto et al. |
| 4,028,186 | A | | 6/1977 | Sakai |
| 4,032,403 | A | | 6/1977 | Sakai et al. |
| 4,487,198 | A | | 12/1984 | Miyake et al. |
| 4,595,418 | A | | 6/1986 | Yoshino |
| 4,816,445 | A | | 3/1989 | Mitsuhashi et al. |
| 5,112,407 | A | * | 5/1992 | Sakai et al. ............ 127/58 |
| 6,063,138 | A | | 5/2000 | Hanna et al. |
| 6,126,962 | A | | 10/2000 | Chaen et al. |

FOREIGN PATENT DOCUMENTS

| EP | 0294093 | 12/1988 |
| EP | 0294093 B1 | 9/1993 |
| EP | 0 850 947 A1 | 7/1998 |
| GB | 1292291 | 11/1969 |
| GB | 1510847 | 7/1975 |
| GB | 2148297 A | 5/1985 |
| JP | 52-136112 | 11/1977 |
| JP | 54-3937 | 1/1979 |
| JP | 54-27325 | 3/1979 |
| JP | 56-28153 | 3/1981 |
| JP | 56-28154 | 3/1981 |
| JP | 57-3356 | 1/1982 |
| JP | 62-51120 | 3/1987 |
| JP | 63-297394 | 12/1988 |
| JP | 06-79316 B2 | 11/1993 |
| JP | 2518646 | 5/1996 |
| JP | 09-110891 A | 4/1997 |
| JP | 2696530 B2 | 9/1997 |

OTHER PUBLICATIONS

Denpu-Tou-Kanren-Kogyo-Bunseki-Hou (Starchey Sugar-Related Industrial Analysis), Edit, by Shokuhin Kagaku Shimbun, Ltd., (1991), pp. 188.
W. Ruland "X-ray Determination of Crystallinity and Diffuse Disorder Scattering" Acta Cryst. (1961), vol. 14, pp. 1180-1185.

* cited by examiner

*Primary Examiner*—Shaojia Anna Jiang
*Assistant Examiner*—Michael C. Henry
(74) *Attorney, Agent, or Firm*—Browdy and Neimark, PLLC

(57) ABSTRACT

The object of the present invention is to provide a powdery product comprising crystalline β-maltose monohydrate which is powderized by spray method, and has a high-solubility in aqueous solvents and a satisfactory handleability, and to its preparation and uses. The present invention solves the above object by establishing a powdery product comprising crystalline β-maltose monohydrate which comprises 7% (w/w) or more but less than 14% (w/w) α-anomeric maltose, and has a crystallinity of 62% or more but less than 72%; a process for producing thereof which comprises the steps of producing a massecuite from an aqueous maltose solution comprising 86% (w/w) or more but less than 93% (w/w) of maltose and 2% (w/w) or more of glucose, on a dry solid basis, powderizing by a spray method, keeping in a relatively low humidity and a relatively high temperature, and further keeping in a relatively high humidity- and a relatively low temperature-condition; and uses thereof for various compositions such as foods, cosmetics, and pharmaceuticals.

8 Claims, 3 Drawing Sheets

POWDERY PRODUCT COMPRISING CRYSTALLINE β-MALTOSE MONOHYDRATE, ITS PREPARATION, AND USES

RELATED APPLICATIONS

This application is a continuation of parent application Ser. No. 10/468,795, nationalized Aug. 22, 2003, now U.S. Pat. No. 6,897,202 which application is the U.S. national stage of international application PCT/JP02/08410, filed Aug. 21, 2002, the contents of which are incorporated herein by reference.

TECHNICAL FIELD

The present invention relates to a powdery product comprising crystalline β-maltose monohydrate (throughout the specification, "crystalline β-maltose monohydrate" is abbreviated as "HCBM" hereinafter, unless specified otherwise), its preparation and uses, and more particularly, to a powdery product comprising HCBM which is powderized by spray method, and having a high-solubility in aqueous solvents and a satisfactory handleability, to its preparation and uses for various compositions such as foods, cosmetics, and pharmaceuticals which are produced by dissolving and incorporating the powdery product into the compositions.

BACKGROUND ART

Traditionally, sucrose has been used in large quantity as a sweetener. Recently, however, sucrose has been being less preferred because of its strong sweetness. Further, sucrose has the defect in the major cause of dental caries.

In recent years, uses of several saccharides have been proposed to solve the defect of sucrose. Particularly, maltose, which is produced from starch, has characteristics such as a relatively low sweetness, less fear of causing dental caries, and good taste in comparison with sucrose. At present, powdery products comprising HCBM, "SUNMALT®" and "SUNMALT S®" are commercialized by Hayashibara Shoji, Inc., Okayama, Japan, as food-grade products, and are expected to be increased in their consumptions.

Powdery products comprising HCBM are usually produced from aqueous solutions comprising maltose as a material by molasses separation, block pulverization, or spray method.

In these methods, molasses separation is a production method for a powdery product comprising the steps of concentrating an aqueous solution comprising maltose as a material, cooling gradually the solution while stirring in the presence of a seed crystal of HCBM to produce a massecuite containing HCBM, separating the crystals formed in molasses by centrifugation, and collecting and drying the crystals. Although a crystalline maltose powder with extremely high-purity is obtainable, this method has the defect in a relatively low yield of HCBM powder because of the production of molasses.

In contrast, block pulverization method is a process for producing a maltose powder, which usually comprises the steps of concentrating an aqueous solution comprising maltose as a material to produce massecuite, solidifying the whole contents, aging, pulverizing, drying, and collecting the resulting powder. Spray method is a process for producing a maltose powder, which usually comprises the steps of concentrating an aqueous solution comprising maltose as a material to produce massecuite, spray-drying the massecuite, aging, and collecting the resulting powder. Although those methods are not able to increase the purity of maltose, they can powderize the whole contents without forming molasses and are advantageous for industrial production.

Particularly, block pulverization method is a process for producing a stable powdery product comprising HCBM, which usually comprises the steps of concentrating an aqueous solution comprising maltose, partially crystallizing HCBM by adding HCBM as a seed crystal to produce massecuite, solidifying the whole contents into a block form, aging, pulverizing, drying, and screening the powder. The product industrially produced by the block pulverization method has been commercialized by Hayashibara Shoji Inc., Okayama, Japan, as "SUNMALT®". By the block pulverization method, all of the maltose can be powderized and is advantageous for industrial production. However, the block pulverization method has the defect of requiring complicated processes of pulverization, drying, and screening as well as requiring a long production period of 5 to 15 days for solidifying massecuites into a block form and for aging.

On the other hand, as disclosed in Japanese Patent Kokai Nos. 3,937/79 and 27,325/79, there has been known that a process for producing a powdery product comprising HCBM by a spray method, which comprises the steps of concentrating an aqueous solution comprising maltose, partially crystallizing HCBM by adding HCBM as a seed crystal to produce a massecuite, powderizing by spray-drying and aging. The spray method is most advantageous for industrial production because it does not require a long term for solidifying massecuites and for aging. However, the spray method requires a three to four day production period and has difficulty in producing powdery products smoothly and continuously.

Thereafter, to improve the above problem, a process for producing a powdery product comprising HCBM, which can be produced in a relatively short time by spray method, has been established by using an aqueous solution containing an extremely high purity maltose with a purity of about 95 w/w % (throughout the specification, "w/w %" is abbreviated as "%" hereinafter, unless specified otherwise) or more, on a dry solid base (d.s.b.); decreasing the contents of saccharides except for maltose, particularly, decreasing the contents of glucose, maltotriose, and saccharides, with a glucose polymerization degree of four or higher, as low as possible. The product has been commercialized by Hayashibara Shoji Inc., Okayama, Japan, as a trade mark of "SUNMALT S®". However, it is revealed that the powdery product comprising HCBM, which is obtainable by spray method, has, unexpectedly, an unsatisfactory solubility in aqueous solvents, that should be improved.

DISCLOSURE OF INVENTION

The present invention was made to overcome the above defect of the spray method as a newly discovered by the present inventors. The object of the present invention is to provide a powdery product comprising HCBM having a high solubility in aqueous solvents and a satisfactory handleability by using a spray method which is advantageous for industrial production and has a relatively low cost, and to its preparation and uses.

To solve the above object, the present inventors studied several properties of powdery products comprising HCBM, which is had been by a spray method. Particularly, the present inventors energetically studied the relationship between the sugar composition of aqueous solutions comprising maltose as a material and the properties of the final powdery products; massecuites, prepared from aqueous solutions comprising maltose and various sugars, were powderized by a spray method. Powdery products comprising HCBM which are obtainable by keeping the powder in a relatively low humidity and high temperature, and then keeping in a relatively high humidity and low temperature were collected, and their several properties such as hygroscopcity, solidification, solubility, content of α-anomeric maltose, and crystallinity were examined in detail.

As a result, the present inventors accomplished the present invention by:

1) finding a powdery product comprising HCBM, powderized by a spray method, which comprises, on a dry solid basis, 86% or more but less than 93% of maltose and 2% or more of glucose, and has a crystallinity of the powdery product of 62% or more but less than 72%, has a satisfactory solubility in aqueous solvents and handleability;

2) establishing a process for producing a powdery product, which comprises the steps of:
   producing a massecuite which comprises hydrous crystalline β-maltose from an aqueous solution comprising, on a dry solid basis, 86% or more but less than 93% of maltose and 2% or more of glucose;
   powderizing the massecuite by a spray method;
   converting the resulting powder into a powder having a high content of α-anomeric maltose by keeping the powder under relatively low humidity and high temperature conditions;
   decreasing the content of α-anomeric maltose to 7%, d.s.b., or more but less than 14%, d.s.b., by keeping the powder under relatively high humidity and low temperature conditions; and
   collecting the resulting powder having a crystallinity of 62% or more but less than 72%; and 3) producing a composition as a powdery product comprising HCBM of above 1) or that obtainable by the process of 2) by dissolving the powdery product in an aqueous solvent.

BEST MODE FOR CARRYING OUT THE INVENTION

Figure 1:
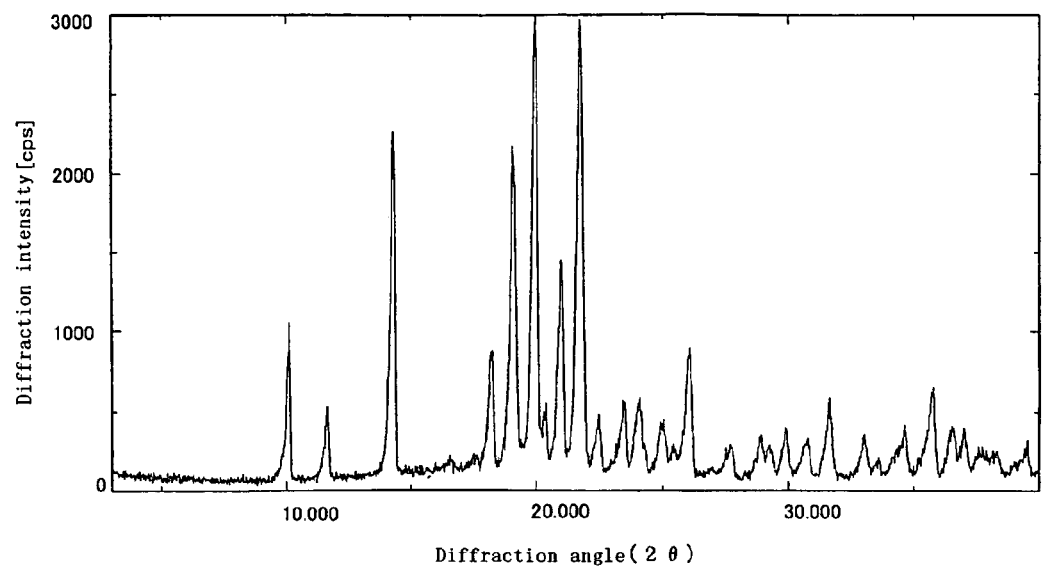
FIG. 1 shows a powdery X-ray diffraction pattern of a HCBM powder having a maltose content of 86.2%, d.s.b., and a crystallinity of 62.1%.

The aqueous solution comprising maltose according to the present invention, which comprises, on a dry solid basis, 86% or more but less than 93% of maltose and 2% or more of glucose, which can be powderized by spray method, and which can be converted into a powdery product comprising HCBM having a crystallinity of 62% or more but less than 72%, can be used as the material of a powdery product comprising HCBM. As disclosed in Japanese Patent Kokai Nos. 3,937/79, 28,153/81, and 3,356/82, and Japanese Patent No. 2,518,646, the process for producing such an aqueous solution comprising maltose is produced by the steps of gelatinizing several kinds of starches by heating, liquefying the gelatinized starches by reacting with an α-amylase (EC 3.2.1.1) or treating with acids or mechanical shearing stress into a solution having a minimum hydrolysis rate, saccharifying the liquefied starch by reacting with β-amylase (EC 3.2.1.2) and starch-debranching enzyme (pullulanase (EC 3.2.1.41) or isoamylase (EC 3.2.1.68)).

The aqueous solution comprising, on a dry solid basis, 86% or more but less than 93% of maltose and 2% or more of glucose, referred to as in the present invention, is produced from starches as described previously. Usually, such a solution optionally comprises maltotriose and saccharides with a glucose polymerization degree of four or higher as other saccharides. It is more desirable to decrease the contents of maltotriose and saccharides with a glucose polymerization degree of four or higher in the aqueous solution comprising maltose because they may inhibit the crystallization of HCBM. Particularly, maltotriose should preferably be less than 2%, d.s.b.

As disclosed in Japanese Patent Kokai No. 28,154/81 and Japanese Patent No. 2,696,530, the contents of maltotriose and saccharides with a glucose polymerization degree of four or higher can be decreased and the content of maltose can be increased by contacting an enzyme, which is capable of hydrolyzing maltotriose and saccharides with a glucose polymerization degree of four or higher, with these saccharides to produce glucose and maltose. The maltotriose and saccharides can be separated and eliminated by ultra filter (UF) membranes, reverse osmosis membranes, and activated charcoals, or by chromatographies using ion-exchange resins as disclosed in Japanese Patent Kokai Nos. 51,120/87 and 79,316/93.

One of the features of the present invention is that a powdery product comprising HCBM having a maltose content of 86% or more but less than 93% and having a satisfactory solubility and handleability can be easily produced by a spray method by applying a series of processes, combined several processes described below, and accelerating the rate of crystallization of maltose from a material, wherein the powdery product has a relatively high content, 7% or more but less than 14%, of saccharides except maltose such as glucose, maltotriose, and saccharides with a glucose polymerization degree of four or higher.

The series of process comprises:

(a) producing a massecuite from an aqueous solution comprising maltose, which has a sugar composition used in the present invention;

(b) powderizing the massecuite by a spray method, more particularly, a spray-drying method using a high pressure nozzle or a rotary disk to produce a powder having a moisture of less than 10%, more preferably, about 5–9%;

(c) converting the resulting powder into a powder having a high content of α-anomeric maltose, preferably, 35% or more, by keeping in a relatively low humidity, preferably, a relative humidity (RH) of lower than 40%, more preferably, lower than 20%, and a high temperature, preferably, higher than 75° C., more preferably, 80–110° C., for 1–4 hours to accelerate the rate of crystallization of maltose;

(d) decreasing the content of α-anomeric maltose to 7% or more but less than 14% by keeping under relatively high humidity, preferably, a RH of higher than 70% or higher, more preferably, 80% or higher, and a low temperature, preferably lower than 50° C., more preferably, 20–45° C., for 5–10 hours; and (e) collecting the resulting powder having a crystallinity of 62% or more but less than 72%.

The following explains the above each process in detail.

In the process (a), a massecuite is produced by the steps of concentrating an aqueous solution comprising maltose, preferably, to give a moisture of 15–30%, adding an appropriate amount of HCBM, usually, 0.1–5%, as a seed crystal, and cooling gradually with stirring. In such a case, the viscosity of the massecuite increased as the increase of the percentage of crystal of HCBM. (hereinafter, the percentage of crystal means the value calculated from the equation described below in the present specification, unless specified otherwise.):

Equation;

(Weight of crystal, d.s.b.)/(Weight of massecuite, d.s.b.)×100

In the process (b), the present inventors found that a powdery product comprising HCBM can be produced easily using a spray method by reducing the viscosity of a high viscosity massecuite comprising HCBM by heating without substantially decreasing the percentage of the crystal. Specifically, the present inventors found that crystals in the massecuite did not dissolve in a relatively short period of time with rising the temperature in some degree, and the decline of percentage of the crystal was not detected practically, whereas the viscosity of the massecuite was reduced immediately with rise in temperature when heated.

It was revealed that the viscosity of the massecuite is reduced by heating without substantially decreasing the percentage of the crystal, preferably, 50,000 cp (throughout the specification, the viscosity (cp) means the value measured on a BH-type rotation viscometer, a rotor of No. 7, and the rotation of 4 rpm hereinafter, unless specified otherwise) or lower, whereby the operation of spraying is facilitated, and the drying is improved efficiently.

Method for rising the temperature is not restricted. Conventional methods, for example, running a warm water in a jacket of a crystallizer containing a massecuite, blowing steam directly into the massecuites in the crystallizer, heating by a regenerator attached between the crystallizer and a transfer pump, etc., can be arbitrarily used. The viscosity of the massecuite should be reduced to the level that enables to spray the massecuite, concretely, 50,000 cp or lower, more preferably, 40,000 cp or lower. For the purpose, it is preferable that the massecuite is heated in a short period of time for avoiding the reduction of the percentage of the crystal, usually at a temperature of 2 to 15° C., preferably, 2 to 10° C.

In the process (c), it can be advantageously adopted to isomerize β-anomeric maltose into α-anomeric maltose by contacting the powder with small amount of anhydrous crystalline α-maltose. There are α- and β-amomeric maltoses as maltose isomers. Anhydrous crystalline α-maltose, HCBM, anhydrous crystalline β-maltose, and α,β-complex crystal in which α-maltose with β-maltose coexists in a contant ratio have been known as crystalline forms.

The term, "comprising 7% (w/w) or more but less than 14% (w/w) of α-anomeric maltose" means the content of α-anomeric maltose in maltose and includes both amorphous and crystalline forms. Generally, maltose comprising 14% or more of α-anomeric maltose has a relatively high content of amorphous maltose or anhydrous crystalline α-maltose. In contrast, maltose comprising less than 7% of α-anomeric maltose has a high content of HCBM or anhydrous crystalline β-maltose because most of the maltose is β-maltose.

In the process (d), the content of α-anomeric maltose in maltose is allowed to decrease to 7% or more but less than 14% by keeping the resulting crystal for about 5 to 10 hours. If necessary, the powder can be advantageously dried by further drying process.

In the process (e), the resulting powdery product comprising HCBM comprises a large amount of a powder having a relatively large particle size, usually, 60% or more of a powder having a particle size of 106 μm or larger, mostly, 40% or more of a powder having a particle size of 150 μm or larger but 300 μm or smaller in a grading analysis (50 grams of a sample was screened for 15 minutes using a JIS Z8801 screen according to the method described in "Denpun-Tou-Kanren-Kogyo-Bunseki-Hou (Starchey Sugar-Related Industrial Analysis)", (in Japanese) pp. 118 ff., Edit. by Shokuhin Kagaku Shimbun, Ltd., 1991). The powder having a particle size of 150 μm or larger but 300 μm or smaller often comprises an aggregate constructed by fines which are produced by the material falling down in a spray-dryer or in a process from aging to the end of drying.

The powdery product comprising HCBM of the present invention, thus obtained, is a powder having a satisfactory solubility in aqueous solvents, preservation stability, fluidity, and handleability.

The aqueous solvents as referred to as in the present invention include water, liquids, pastes, semi-solids, and solids which contain a relatively large amount of water, which can dissolve and comprise a powdery product of HCBM. Particularly, solvents comprising, for example, sugar, starch, fat, protein, polyphenol, emulsifier, etc.; concretely, for example, pastes, dough, and noodles, prepared from a powdery product comprising starch in a relatively high amount such as gelatinized starch, which is used to "gyuhi" (a rice paste) and "mochi-gashi" (a rice paste cake), wheat flour, rice powder, fresh "an" (a bean-jam), fish meat, minced meat, beaten egg, milk cream, fermented milk, peanut paste, fruit pulp, vegetable pulp, sugar syrup, condensed extract, etc., can be used as aqueous solvents having a relatively high viscosity.

Since the powdery product comprising HCBM of the present invention has a satisfactory solubility in the above aqueous solvents having a relatively high viscosity, it can be also advantageously used in aqueous solvents having a relatively low viscosity. Further, since it had a satisfactory sweetness with a good quality and an activity to prevent the formation of dextran which is one of the causes of dental caries, a powdery product comprising HCBM of the present invention can be suitably used as a sweetener which does not cause dental caries.

The powdery product comprising HCBM of the present invention can be advantageously used as a sugar-coating agent for tablets in combination with binders such as pullulan, hydroxyethyl starch, and polyvinylpyrrolidone. Furthermore, the powdery product comprising HCBM of the present invention has useful properties of osmosis-controlling ability, filler-imparting ability, gloss-imparting ability, moisture-retaining ability, viscosity, crystallization-preventing ability for other saccharides, retrogradation-preventing ability of gelatinized starch, etc.

Thus, the powdery product comprising HCBM of the present invention can be advantageously used as a sweetener, taste-improving agent, flavor-improving agent, quality-improving agent, stabilizer, filler, etc., in a variety of compositions such as food products, feeds, pet foods, cosmetics, pharmaceuticals, tobaccos, and cigarettes.

The powdery product comprising HCBM of the present invention can be used as a seasoning to sweeten various materials. If necessary, it can be advantageously used in combination with one or more other sweeteners, for example, powdery syrup, glucose, fructose, lactose, lactosucrose, sucrose, trehalose, isomerized sugar, honey, maple sugar, isomaltooligosaccharide, galactooligosaccharide, fructooligosaccharide, sorbitol, maltitol, lactitol, dihydrochalcone, stevioside, α-glycosyl stevioside, rebaudioside, glycyrrhizin, L-aspartyl L-phenylalanine methyl ester, sucralose, acesulfame K, saccharine, glycine and alanine; and fillers such as dextrin, starch, sucrose, and lactose.

The powdery product comprising HCBM of the present invention can be arbitrarily used intact or, if necessary, in combination with one or more appropriate substances such as fillers, excipients, binders, sweeteners, etc., and they formed into products with different shapes such as granules, spheres, sticks, plates, cubes, tablets, films, and sheets.

The sweetness of the powdery product comprising HCBM of the present invention well harmonizes with other tastable materials having sour-, salty-, astringent-, delicious-, and bitter-taste; and can be favorably used to sweeten and/or improve the taste, and the quality of food products in general, for example, amino acids, peptides and the like, a soy sauce, powdered soy sauce, miso, "funmatsu-miso" (a powdered miso), "moromi" (a refined sake), "hishio" (a refined soy sauce), "furikake" (a seasoned fish meal), mayonnaise, dressing, vinegar, "sanbai-zu" (a sauce of sugar, soy sauce and vinegar), "funmatsu-sushi-zu" (powdered vinegar for sushi), "chuka-no-moto" (an instant mix for Chinese dish), "tentsuyu" (a sauce for Japanese deep fat fried food), "mentsuyu" (a sauce for Japanese vermicelli), sauce, catsup, "yakiniku-no-tare" (a sauce for Japanese grilled meat), curry roux, instant stew mix, instant soup mix, "dashi-no-moto" (an instant stock mix), nucleic acid seasoning, mixed seasoning, "mirin" (a sweet sake), "shin-mirin" (a synthetic mirin), table sugar, and coffee sugar. Also, the powdery product comprising HCBM of the present invention can be advantageously used to "wagashi" (Japanese cakes) such as "senbei" (a rice cracker), "arare" (a rice cake cube), "okoshi" (a millet and rice cake), "mochi" (a rise paste) and the like, "manju" (a bun with a bean-jam), "uiro" (a sweet rice jelly), "an" (a bean-jam) and the like, "yokan" (a sweet jelly of beans), "mizu-yokan" (a soft azuki-bean jelly), "kingyoku" (a kind of yokan), jelly, pao de Castella, and "amedama" (a Japanese toffee); Western confectioneries such as a bun, biscuit, cracker, cookie, pie, pudding, butter cream, custard cream, cream puff, waffle, sponge cake, doughnut, chocolate, chewing gum, caramel, and candy; frozen desserts such as an ice cream and sherbet; syrups such as a "kajitsu-no-syrup-zuke" (a preserved fruit) and "korimitsu" (a sugar syrup for shaved ice); pastes such as a flour paste, peanut paste, fruit paste, and spread; processed fruits and vegetables such as a jam, marmalade, "syrup-zuke" (fruit pickles), and "toka" (conserves); pickles and pickled products such as a "fukujin-zuke" (red colored radish pickles), "bettara-zuke" (a kind of whole fresh radish pickles), "senmai-zuke" (a kind of sliced fresh radish pickles), and "rakkyo-zuke" (pickled shallots); premix for pickles and pickled products such as "takuan-zuke-no-moto" (a premix for pickled radish), and "hakusai-zuke-no-moto" (a premix for fresh white rape pickles); meat products such as a ham and sausage; products of fish meat such as a fish ham, fish sausage, "kamaboko" (a steamed fish paste), "chikuwa" (a kind of fish paste), and "tenpura" (a Japanese deep-fat fried fish paste); "chinmi" (relish) such as a "uni" (urchin), "ika-no-shiokara" (salted guts of squid), "su-konbu" (processed tangle), "saki-surume" (dried squid strips), "fuguno-mirin-boshi" (a dried mirin-seasoned swellfish); "tsukudani" (foods boiled down in soy sauce) such as those of laver, edible wild plants, dried squid, small fish, and shellfish; daily dishes such as a "nimame" (cooked beans), potato salad, and "konbu-maki" (a tangle roll); milk products such as yoghurt and cheese; canned and bottled products such as those of fish meat, meat, fruit, and vegetable; alcoholic beverages such as a sake, synthetic sake, liqueur, and Western liquor; soft drinks such as a coffee, tea, cocoa, juice, carbonated beverage, sour milk beverage, and beverage containing a lactic acid bacterium; instant food products such as instant pudding mix, instant hot cake mix, "sokuseki-shiruko" (an instant mix of azuki-bean soup with rice cake), and instant soup mix; and other foods and beverages such as solid foods for babies, foods for therapy, drinks, peptide foods, frozen foods and healthy foods.

The powdery product comprising HCBM of the present invention can be arbitrarily used to improve the taste preference of feeds and pet foods for animals and pets such as domestic animals, poultry, honey bees, silk worms, and fishes; and also it can be advantageously used as a sweetener and taste-improving agent, taste-curing agent, quality-improving agent, and stabilizer in other products in a paste or liquid form such as tobacco, cigarette, tooth paste, lipstick, rouge, lip cream, internal liquid medicine, tablet, troche, cod-liver oil in the form of drop, oral refrigerant, cachou, and gargle.

By using the powdery product comprising HCBM of the present invention as a quality-improving agent or stabilizer in health foods and pharmaceuticals containing effective ingredients, active ingredients, or biologically active substances, health foods and pharmaceuticals in a liquid, paste, or solid form, which have a satisfactorily-high stability and quality, health foods and pharmaceuticals can be arbitrary prepared. Examples of such effective ingredients and biologically active substances are lymphokines such as α-, β-, and γ-interferons, TNF-α, TNF-β, macropharge migration inhibitory factor, colony-stimulating factor, transfer factor, and interleukin; hormones such as insulin, growth hormone, prolactin, erythropoietin, and follicle-stimulating hormone; biological preparations such as BCG vaccine, Japanese encephalitis vaccine, measles vaccine, live polio vaccine, small pox vaccine, tetanus toxoid, Trimeresurus antitoxin, and human immunoglobulin; antibiotics such as penicillin, erythromycin, chloramphenicol, tetracycline, streptamycin, and kanamycin sulfate; vitamins such as thiamin, riboflavin, L-ascorbic acid, α-glycosyl L-ascorbic acid, cod liver oil, carotenoide, ergosterol, tocopherol, rutin, α-glycosyl rutin, narindin, α-glycosyl narindin, hesperidin, and α-glycosyl hesperidin; enzymes such as lipase, elastase, urokinase, protease, α-amylase, isoamylase, glucanase, and lactase; extracts such as ginseng extract, bamboo grass extract, plum extract, pine leaf extract, turtle extract, chlorella extract, aloe extract, and propolis extract; living microorganism such as virus, lactic acid bacterium, and yeast; and royal jelly.

The methods for incorporating the powdery product comprising HCBM of the present invention into the aforesaid compositions are those which can incorporate the powdery product comprising HCBM into a variety of compositions before completion of their processings, and the method can be appropriately selected among the following conventional methods; mixing, dissolving, melting, soaking, penetrating, dispersing, applying, coating, spraying, injecting, crystallizing, and solidifying. The amount of the powdery product comprising HCBM to be preferably incorporated into the final compositions is usually in an amount of 1% or higher, desirably, 2% or higher, more desirably 5 to 99%, d.s.b.

The following experiment concretely explains the present invention.

EXPERIMENT

Effect of Sugar Compositions of Material on the Physical Properties of Various Powdery Products Comprising HCBM Effect of material sugar compositions on the physical properties of various powdery products comprising HCBM, which were produced by a spray method, was examined. Powdery products comprising HCBM, produced by the steps of preparing various aqueous solutions comprising material maltose and having different sugar compositions, and spraying, were used as sample powders for the test. Aqueous solutions comprising maltose, having various sugar compositions, were prepared by using a commercially-available purified maltose ("SUNMALT®" commercialized by Hayashibara Shoji, Inc., Okayama, Japan) or mixtures of the purified maltose, glucose (special reagent grade, commercialized by Wako Pure Chemicals Industries, Ltd., Oksaka, Japan), maltotriose, maltotetraose, and/or maltopentaose (which are all reagent grades, produced by Hayashibara Biochemical Laboratories, Inc., Okayama, Japan).

Powdery products comprising HCBM were prepared by a spray method as follows. An aqueous solution comprising maltose as a material was concentrated to give a moisture content of 25%, transferred to a crystallizer, admixed with 1% of HCBM as a seed crystal, and HCBM was partially crystallized by cooling gradually to 30° C. under gentle stirring conditions over 12 to 18 hours to obtain a massecuite. The percentage of the crystal of the massecuite was 36% to 43%. After the crystallization, the massecuite with a viscosity of higher than 50,000 cp was heated before running using a high-pressure pump to decrease its viscosity to about 45,000 cp without decreasing the percentage of the crystal, and sprayed by a pressurized nozzle. The conditions for spray-drying were as follows: The temperature of the hot air for drying was set to 75° C.; the blow mode was set to vertical, descendent, and parallel blow in the spray-dryer; and the flow was set to allow the moisture of the dried powder taken out from the spray-dryer to be 8.5%. The resulting powder was immediately allowed to contact with 0.2% of anhydrous crystalline α-maltose by mixing, and kept at 90° C. for two hours under a relative humidity (RH) of 20%. Subsequently, the powder was kept at 30° C. and RH 80% for five hours for aging to obtain a powdery product comprising HCBM. The resulting powder was subjected to tests for physical properties described below.

A purified maltose ("SUNMALT®" commercialized by Hayashibara Shoji, Inc., Okayama, Japan), a reagent grade HCBM ("MALTOSE HHH" produced by Hayashibara Biochemical Laboratories, Inc., Okayama, Japan), and an anhydrous crystalline α-maltose ("FINETOSE®" commercialized by Hayashibara Shoji, Inc., Okayama, Japan) were used as controls in the tests for physical properties.

The tests for physical properties were carried out using the methods described below:

A. Sugar Composition Analysis

Sugar composition was analyzed by liquid chromatography (HPLC) using "KS-801", a column commercialized by Showa Denko K. K., Tokyo, Japan, or "CH04SS", a column commercialized by Mitsubishi Chemical Corp., Tokyo, Japan, and calculated from the ratio of peak area in the chromatogram.

B. Hygroscopicity

An open aluminum cup containing a sample was placed in a desiccator, set at a RH of 75.2% (equilibrated with a saturated sodium chloride aqueous solution), kept at 25° C. for three days, and then weighted. Hygroscopicity was expressed with percentage (%) of the increased weight to the initial weight of the sample.

C. Solidification

A sample in the aluminum cup, taken out after keeping three days in the above hygroscopicity test, was macroscopically observed. Solidification was judged from the appearance of the sample whether it was solidified or not by adsorbing moisture.

D. Solubility (i) Solubility in Water

Five milliliters of deionized water with 25° C. was placed in a plastic tube, and admixed with one gram of each powdery product comprising HCBM, having different sugar compositions at once. The tube was sealed when the powder was sunk in water and kept at 25° C. in an incubator. The dissolution of the powder was macroscopically observed every other 20 minutes. Solubility in water was estimated by the time (minute) that needed to dissolve the powder into a clear solution. The powder showing shorter time to disappear was judged to have a satisfactory solubility as a criterion.

(ii) Solubility in an Aqueous Solution Comprising Dextrin

Five milliliters of a sticky aqueous solution comprising dextrin ("PINEDEX #1, commercialized by Matsutani Chemical Industry Co., Ltd., Hyogo, Japan) with a concentration of 17% was put in a plastic tube, and admixed with one gram of each powdery product comprising HCBM, having different sugar compositions in the same manner described in (i). The tube was sealed when the powder was sunk in water and kept at 25° C. in an incubator. The criterion of the estimation was used with the same one described in (i).

E. Analysis of Anomeric Isomers of Maltose

A sample was dissolved in anhydrous pyridine, converted into TMS-derivative, and then analyzed by gas chromatography using "2% OV-17 CHROMOSORB W (AW-DMCS)", a pre-packed column commercialized by GL Sciences, Tokyo, Japan. The ratio of α- and β-anomeric maltose was calculated from the peak area in the chromatogram.

F. Crystallinity

Crystallinity of powder was measured by the method of Ruland (*Acta Crystallographica*, Vol. 14, p. 1180, 1961) based on a powdery X-ray diffraction pattern using "GEIGER-FLEX RDA-II B", an X-ray diffractometer (Cu, Kα-ray) commercialized by Rigaku Corp., Tokyo, Japan. Among the powders measured, representative powdery X-ray diffraction patterns were shown in FIGS. 1 to 5.

Sugar compositions of each aqueous solution comprising maltose as materials and each result of the tests, hygroscopicity, solidification, solubility, content of α-anomeric maltose, and crystallinity of each powders are summarized in Table 1 as the physical properties of the powdery products comprising HCBM.

content of 99.6%, a high crystallinity of 82.6%, no hygroscopicity and no substantial solidification. However, it had an unsatisfactory solubility in aqueous solvents. "FINETOSE®", different from other samples, is an anhydrous

TABLE 1

Figure 2:
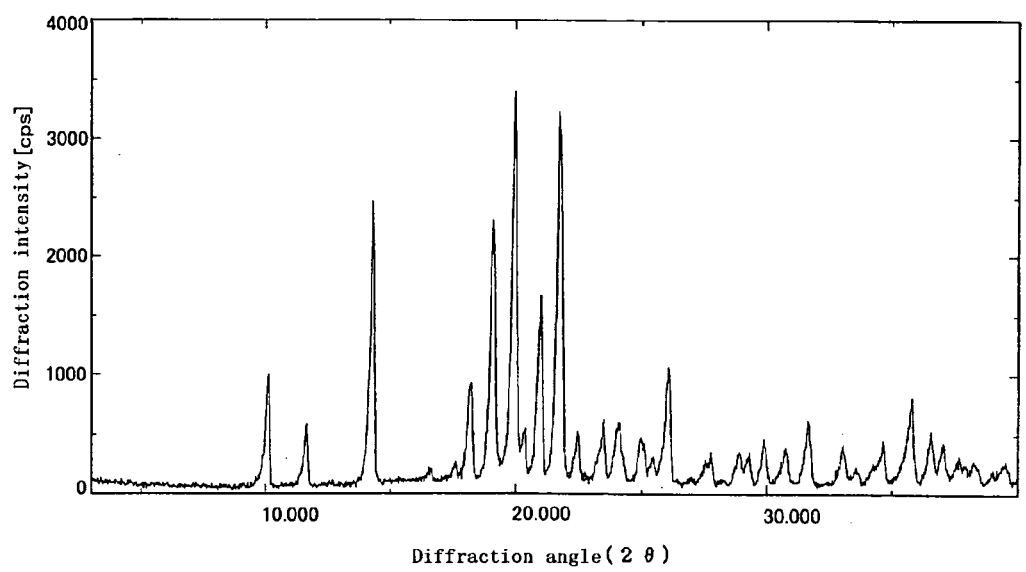
FIG. 2 shows a powdery X-ray diffraction pattern of a HCBM powder having a maltose content of 91.3%, d.s.b., and a crystallinity of 70.8%.
Figure 3:
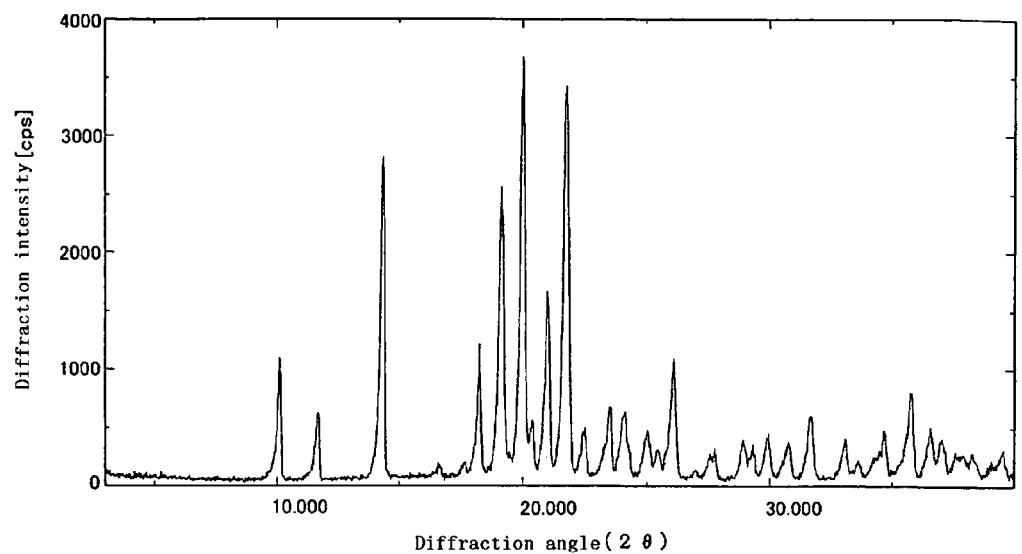
FIG. 3 shows a powdery X-ray diffraction pattern of a purified maltose specimen, "SUNMALT S®", having a maltose content of 95.0%, d.s.b., and a crystallinity of 74.5%.
Figure 4:
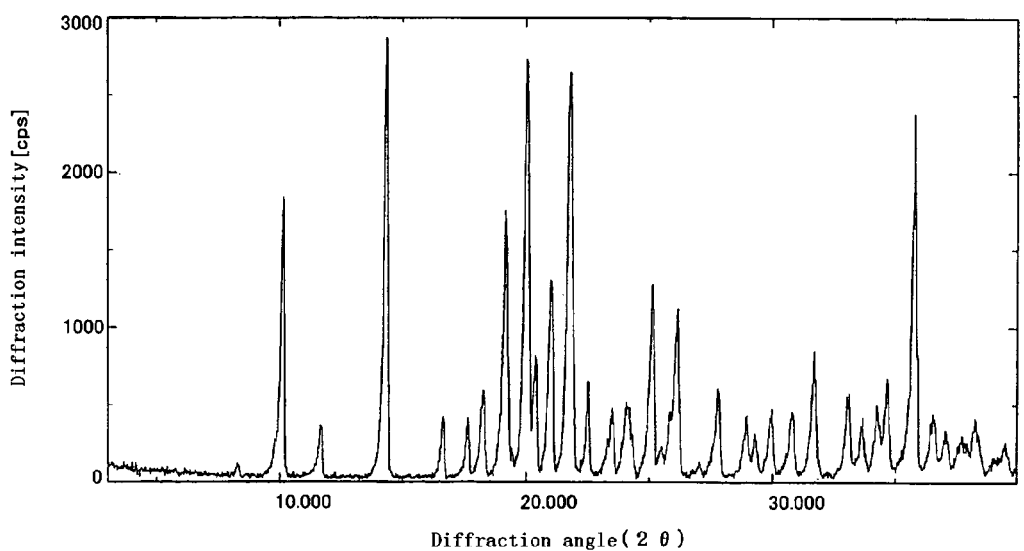
FIG. 4 shows a powdery X-ray diffraction pattern of a reagent-grade HCBM, trade name "MALTOSE HHH", having a maltose content of 99.6%, d.s.b., and a crystallinity of 82.6%.
Figure 5:
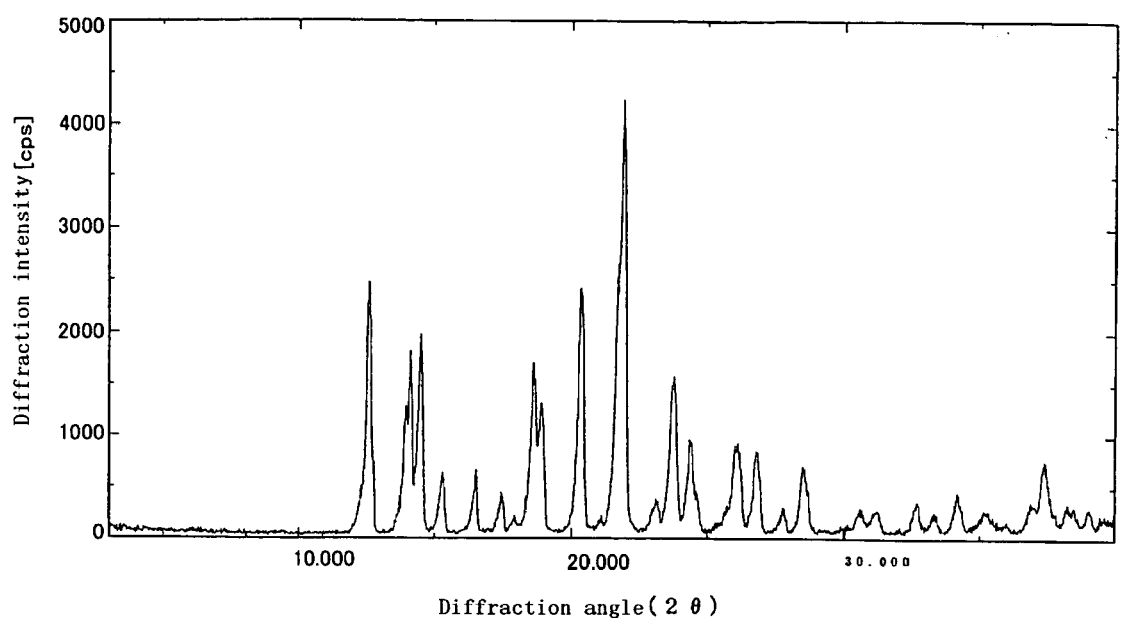
FIG. 5 shows a powdery X-ray diffraction pattern of an anhydrous crystalline α-maltose, "FINETOSE®", having a maltose content of 98.5%, d.s.b., and a crystallinity of 76.3%.

| No. | Sugar composition (%) | | | | Hygroscopicity (%) | Solidification | Solubility (min) | | α-Maltose (%) | Crystallinity (%) | Powdery X-ray diffraction |
|---|---|---|---|---|---|---|---|---|---|---|---|
| | G1 | G2 | G3 | G4≦ | | | Water | Dextrin solution | | | |
| 1 | 4.9 | 82.4 | 4.1 | 8.6 | 6.4 | + | 20 | 80 | 19.2 | 48.8 | |
| 2 | 4.5 | 84.2 | 3.2 | 8.1 | 4.9 | + | 20 | 80 | 16.7 | 56.7 | |
| 3 | 4.2 | 86.2 | 1.9 | 7.7 | 2.8 | − | 20 | 80 | 13.8 | 62.1 | FIG. 1 |
| 4 | 3.0 | 89.3 | 1.6 | 6.1 | 2.3 | − | 20 | 80 | 10.5 | 69.0 | |
| 5 | 4.0 | 91.3 | 0.9 | 3.8 | 1.9 | − | 20 | 80 | 9.8 | 70.8 | FIG. 2 |
| 6 | 2.3 | 92.8 | 0.6 | 4.3 | 1.5 | − | 20 | 80 | 7.8 | 71.4 | |
| 7 | 1.7 | 94.1 | 1.9 | 2.3 | 1.3 | − | 40 | 120 | 6.8 | 73.6 | |
| 8 | 0.8 | 95.0 | 2.0 | 2.2 | 1.2 | − | 40 | 120 | 6.2 | 74.5 | FIG. 3 |
| 9 | 0.1 | 99.6 | 0.2 | 0.1 | 1.0 | − | 180≦ | 180≦ | 4.4 | 82.6 | FIG. 4 |
| 10 | 0.5 | 98.5 | 0.5 | 0.5 | 6.8 | + | 180≦ | 180≦ | 95.6 | 76.3 | FIG. 5 |

Note:
The symbol "G4≦" means oligosaccharides with a glucose polymerization degree of four or higher.
No. 8: A purified maltose, "SUNMALT S ®"
No. 9: A reagent grade hydrous crystalline β-maltose, "MALTOSE HHH"
No. 10: An anhydrous crystalline α-maltose, "FINETOSE ®"

As evident from the results in Table 1, it was revealed that the powdery products comprising HCBM, obtained from the test Nos. 3 to 6 by the spray method, which comprised 86%, d.s.b., or more but less than 93%, d.s.b., of maltose, 2%, d.s.b., or more of glucose, maltotriose, and oligosaccharides with a glucose polymerization degree of four or higher; and which comprised 7% or more but less than 14% of α-anomeric maltose as isomer of maltose, having crystallinity of 62% or more but less than 72%, had low hygroscopicity, no substantial solidification, satisfactory preservation stability and handleability. Further, it was also revealed that these powdery products had satisfactory solubility in aqueous solvents such as water and sticky aqueous solutions comprising dextrin.

In contrast, powdery products comprising HCBM, obtained from the test Nos. 1 and 2 by the spray method, which comprised a relatively low maltose content of 82.4% or 84.2%, and more than 14% of α-anomeric maltose as an isomer of maltose and a crystallinity of less than 62%, had a satisfactory solubility in aqueous solvents. However, they were unstable powders having a relatively high hygroscopicity, solidification, and an unsatisfactory preservation stability.

While a powdery product comprising HCBM, obtained from the test No. 7 by the spray method, which comprised a relatively high maltose content of 94.1%, and a relatively low content, less than 7%, of α-anomeric maltose as an isomer of maltose, having crystallinity of more than 72%, had an unsatisfactory solubility in aqueous solvents, though they had a low hygroscopicity, substantially no solidification.

"SUNMALT S®" of the test No. 8, used as a control, is a powder obtained by the spray method. However, it had an unsatisfactory solubility in aqueous solvents though it had a relatively high maltose content of 95.0%, a relatively high crystallinity of 74.5%, no hygroscopicity and no substantial solidification. "MALTOSE HHH" of the test No. 9 is a crystalline powder obtained from a massecuite by a molasses-separation method. The powder is a product comprising maltose having an extremely high purity, high maltose crystalline α-maltose powder. Since the powder has a high content of α-anomeric maltose, the properties of the powder are fairly different from other powders containing mainly hydrous crystalline β-maltose. It is an unstable powder having a high hygroscopicity, heavy solidification, unsatisfactory preservation stability and solubility in aqueous solvents.

From the results described above, it was revealed that a powdery product comprising HCBM having a satisfactory solubility in aqueous solvents and handleability can be obtained by using an aqueous solution comprising 86% or more but less than 93% of maltose, and 2% or more of glucose, d.s.b., as a material, and produced by a series of processes of the present invention in the case of producing a powdery product comprising HCBM by a spray method.

Therefore, a powdery product comprising HCBM which comprises 86% or more but less than 93% of maltose, and 2% or more of glucose, d.s.b., and having a crystallinity of 62% or more but less than 72%, which is obtainable by the present invention, has a satisfactory solubility in aqueous solvents and handleability, and can be produced in a relatively high yield. In addition, time for dissolving the product in aqueous solvents can be reduced in comparison with conventional products. Therefore, the powdery product comprising HCBM is significantly important for industrial uses.

The following examples concretely explain the present invention. However, the present invention is not restricted thereunto:

EXAMPLE A-1-a

Preparation of Aqueous Maltose Solution

A suspension, containing one part by weight of potato starch and four parts by weight of water, was admixed with "SPITASE HS", a bacterial liquefying α-amylase commercialized by Nagase & Co., Ltd., Osaka, Japan, and gelatinized by heating at 90° C. The resulting liquefied starch solution having a DE of 1.8 was obtained by heating the gelatinized solution immediately to 130° C. to stop the enzyme reaction. The liquefied starch solution was cooled to 55° C. rapidly, admixed with 100 units/g-starch of a starch-debranching enzyme, isoamylase prepared by culturing a bacterium of the genus *Pseudomonas*, which is commercialized by Hayashibara Biochemical Laboratories Inc., Okayama, Japan, 50 units/g-starch of "#1500", β-amylase from soybean commercialized by Nagase & Co, Ltd., Osaka, Japan, and 10 units/g-starch of "MALTOGENASE", a maltose-forming α-amylase commercialized by Novo Nordisk A/S, Bagsværd, Denmark, and saccharified for 40 hours with keeping the pH at 5.0. The saccharified solution was purified in a usual manner by decoloration using activated charcoal and desalting using an ion-exchanger resin, and then concentrated under reduced pressure to obtain a maltose solution. Sugar composition of the maltose solution was 3.8% of glucose, 92.5% of maltose, 1.1% of maltotriose, and 2.6% of maltotetraose or more.

EXAMPLE A-1-b

Preparation of Powdery Product Comprising HCBM

An aqueous solution comprising maltose, obtained in Example A-1-a, was concentrated to give a moisture content of 29%, transferred to a crystallizer, and admixed with 1% of HCBM as a seed crystal. The massecuite was gradually cooled under gentle stirring conditions to 29° C., and HCBM was partially crystallized over about 12 hours. The percentage of the crystal was 37%. The massecuite obtained from above crystallization was run using a high-pressure pump and sprayed in a spray-dryer using a rotary disk. The conditions for drying were set as below: the temperature of the hot air for drying was set to 70° C.; the blow mode was set to vertical, descendent, and parallel blow in the spray-dryer; and the flow was set to give the moisture of 7.5% of the dried powder taken out from the spray-dryer.

The resulting powder was immediately allowed to contact with 0.2% of anhydrous crystalline α-maltose by mixing, and kept at 80° C. and relative humidity (RH) of 20% for three hours. Subsequently, the powder was kept at 30° C. and RH 80% for five hours for aging, and a powdery product comprising HCBM having the crystallinity of 71.4% and moisture of 6.1% was obtained in a yield of 96%, d.s.b., to the material potato starch. The powder comprised 92.5%, d.s.b., of maltose, 3.8% of glucose, 1.1% of maltotriose, and 2.6% of saccharides with a glucose polymerization degree of four or higher, and comprised 7.8% of α-anomeric maltose as an isomer of maltose, and has a satisfactory solubility to aqueous solvents. The powder has an insubstantial hygroscopicity under the preservation conditions at 25° C. and RH 75.2%, a satisfactory preservation stability, fluidity, and handleability. The powder comprised a powder constructed by cohesion of particles, and comprised 41% of powder with a diameter larger than 150 μm but 300 μm or less in a grading analysis.

Since the powder has a satisfactory solubility to aqueous solvents, it can be advantageously used by allowing to dissolve in pastes, semi-solids, and solids as well as water and liquids containing relatively large amount of water in various compositions such as food products, tobacco, cigarettes, feeds, pet foods, cosmetics, and pharmaceuticals as a sweetener, taste-improving agent, quality-improving agent, stabilizer, discoloration-preventing agent, filler, excipient, and binder. Further, The powder can be arbitrarily used intact or, if necessary, after mixing with fillers, excipients, binders, etc., and them formed into products with different shapes such as granules, spheres, sticks, plates, cubes, tablets, etc.

EXAMPLE A-2-a

Preparation of Aqueous Maltose Solution

A suspension, containing one part by weight of corn starch and three parts by weight of water, was admixed with "SPITASE HS", a bacterial liquefying α-amylase commercialized by Nagase & Co., Ltd., Osaka, Japan, and gelatinized by heating at 90° C. The resulting liquefied starch solution having a DE of 2.5 was obtained by heating the gelatinized solution immediately to 130° C. to stop the enzyme reaction. The liquefied starch solution was cooled to 55° C. rapidly, admixed with 50 units/g-starch of a starch-debranching enzyme, isoamylase prepared by culturing a bacterium of the genus *Pseudomonas*, which is commercialized by Hayashibara Biochemical Laboratories Inc., Okayama, Japan, and 20 units/g-starch of "#1500", β-amylase from soybean commercialized by Nagase & Co, Ltd., Osaka, Japan, and saccharified for 40 hours with keeping the pH at 5.0. A saccharified solution comprising maltose with a high-purity, having a maltose content of 84.6%, d.s.b., was obtained. Sugar composition of the maltose saccharified solution was 3.5% of glucose, 84.6% of maltose, 8.2% of maltotriose, and 3.7% of maltotetraose or more.

The saccharified solution was further admixed with 50 units/g-saccharide of "Taka-amylaseA", an α-amylase, and the enzyme reaction was further proceeded for 20 hours with keeping the pH at 5.5. The resulting saccharified solution was purified in a usual manner by decoloration using activated charcoal and desalting using an ion-exchanger resin, and then concentrated under reduced pressure to obtain a maltose solution. Sugar composition of the maltose solution was 5.6% of glucose, 91.2% of maltose, 1.3% of maltotriose, and 1.9% of maltotetraose or more.

EXAMPLE A-2-b

Preparation of Powdery Product Comprising HCBM

An aqueous solution comprising maltose, obtained in Example A-2-a, was concentrated to give a moisture content of 26%, transferred to a crystallizer, and admixed with 1% of HCBM as a seed crystal. The massecuite was gradually cooled under gentle stirring conditions to 30° C., and HCBM was partially crystallized over about 14 hours. The percentage of the crystal was 41%. The massecuite obtained from above crystallization was run using a high-pressure pump and sprayed in a spray-dryer using a rotary disk. The conditions for drying were set as below: the temperature of the hot air for drying was set to 75° C.; the blow mode was set to vertical, descendent, and parallel blow in the spray-dryer; and the flow was set to give the moisture of 8.5% of the dried powder taken out from the spray-dryer.

The resulting powder was immediately allowed to contact with 0.2% of anhydrous crystalline α-maltose by mixing, and kept at 90° C. and relative humidity (RH) of 25% for two hours. Subsequently, the powder was kept at 30° C. and RH 80% for five hours for aging, and a powdery product comprising HCBM having the crystallinity of 70.4% and moisture of 6.1% was obtained in a yield of 95%, d.s.b., to the material corn starch. The powder comprised 91.2%, d.s.b., of maltose, 5.6% of glucose, 1.3% of maltotriose, and 1.9% of saccharides with a glucose polymerization degree of four or higher, and comprised 9.2% of α-anomeric maltose as an isomer of maltose, and has a satisfactory solubility to aqueous solvents. The powder has an insubstantial hygroscopicity under the preservation conditions at 25° C. and RH 75.2%, a satisfactory preservation stability, fluidity, and handleability. The powder comprised a powder constructed by cohesion of particles, and comprised 47% of powder with a diameter larger than 150 μm but 300 μm or less in a grading analysis.

Since the powder has a satisfactory solubility to aqueous solvents, it can be advantageously used by allowing to dissolve in pastes, semi-solids, and solids as well as water and liquids containing relatively large amount of water in various compositions such as food products, tobacco, cigarettes, feeds, pet foods, cosmetics, and pharmaceuticals as a sweetener, taste-improving agent, quality-improving agent, stabilizer, discoloration-preventing agent, filler, excipient, and binder. Further, The powder can be arbitrarily used intact or, if necessary, after being mixed with fillers, excipients, binders, etc., it can then be formed into products with different shapes such as granules, spheres, sticks, plates, cubes, tablets, etc.

EXAMPLE A-3-a

Preparation of Aqueous Maltose Solution

A suspension, containing one part by weight of corn starch and seven parts by weight of water, was admixed with "SPITASE HS", a bacterial liquefying α-amylase commercialized by Nagase & Co., Ltd., Osaka, Japan, and gelatinized by heating at 90° C. The resulting liquefied starch solution having a DE of 4.3 was obtained by heating the gelatinized solution immediately to 130° C. to stop the enzyme reaction. The liquefied starch solution was cooled to 55° C. rapidly, admixed with 50 units/g-starch of a starch-debranching enzyme, isoamylase prepared by culturing a bacterium of the genus *Pseudomonas*, which is commercialized by Hayashibara Biochemical Laboratories Inc., Okayama, Japan, and 20 units/g-starch of "#1500", β-amylase from soybean commercialized by Nagase & Co, Ltd., Osaka, Japan, and saccharified for 40 hours with keeping the pH at 5.0. A saccharified solution having a maltose content of 84.6%, d.s.b., was obtained. The saccharified solution was purified in a usual manner by decoloration using activated charcoal and desalting using an ion-exchanger resin, and then concentrated under reduced pressure to obtain a maltose solution, having a sugar concentration of 45%, as a material for chromatographic separation.

"AMBERLITE XT-1007 (Na$^+$-form, crosslinking degree 6%)", an alkaline-metal strong acid cation-exchanger resin commercialized by Japan Organo Co., Ltd., Tokyo, Japan, was used as a resin for chromatographic separation. The resin was packed into two jacketed-stainless steel columns having a diameter of 5.4 cm, which were then cascaded in series to give a total gel bed depth of 10 m.

Under the conditions of keeping the inner column temperature at 55° C., the saccharide solution as material was fed to the columns in a volume of 5% (v/v) and fractionated by feeding to the columns hot water heated to 55° C. at an SV (space velocity) of 0.3 to separate and eliminate high maltotriose content fractions, and then collected the high maltose content fractions comprising maltose in high content and other oligosaccharides. Subsequently, the saccharified solution was purified in a usual manner by decoloration using activated charcoal and desalting using an ion-exchanger resin, and then concentrated under reduced pressure to obtain a solution comprising maltose. Sugar composition of the maltose solution was 6.0% of glucose, 90.1% of maltose, 0.8% of maltotriose, and 3.1% of maltotetraose or more.

EXAMPLE A-3-b

Preparation of Powdery Product Comprising HCBM

An aqueous solution comprising maltose, obtained in Example A-3-a, was concentrated to give a moisture content of 24%, transferred to a crystallizer, and admixed with 1% of HCBM as a seed crystal. The massecuite was gradually cooled under gentle stirring conditions to 29° C., and HCBM was partially crystallized over about 15 hours. The percentage of the crystal was 40%. Since the massecuite obtained from above crystallization has a relatively high viscosity, the viscosity was decreased to about 40,000 cp by heating without decreasing the percentage of the crystal when the massecuite was run using a high-pressure pump, and the massecuite was sprayed in a spray-dryer using a pressurized nozzle. The conditions for drying were set as below: the temperature of the hot air for drying was set to 75° C.; the blow mode was set to vertical, descendent, and parallel blow in the spray-dryer; and the flow was set to give the moisture of 9.0% of the dried powder taken out from the spray-dryer.

The resulting powder was immediately allowed to contact with 0.2% of anhydrous crystalline α-maltose by mixing, and kept at 85° C. and relative humidity (RH) of 20% for two hours. Subsequently, the powder was kept at 35° C. and RH 75% for five hours for aging, and a powdery product comprising HCBM having the crystallinity of 69.0% and moisture of 6.4% was obtained in a yield of 89%, d.s.b., to the material corn starch. The powder-comprised 90.1%, d.s.b., of maltose, 6.0% of glucose, 0.8% of maltotriose, and 3.1% of saccharides with a glucose polymerization degree of four or higher, and comprised 9.9% of α-anomeric maltose as an isomer of maltose, and has a satisfactory solubility to aqueous solvents. The powder has an insubstantial hygroscopicity under the preservation conditions at 25° C. and RH 75.2%, a satisfactory preservation stability, fluidity, and handleability. The powder comprised a powder constructed by cohesion of particles, and comprised 51% of powder with a diameter larger than 150 μm but 300 μm or less in a grading analysis.

Since the powder has a satisfactory solubility to aqueous solvents, it can be advantageously used by allowing to dissolve in pastes, semi-solids, and solids as well as water and liquids containing relatively large amount of water in various compositions such as food products, tobacco, cigarettes, feeds, pet foods, cosmetics, and pharmaceuticals as a sweetener, taste-improving agent, quality-improving agent, stabilizer, discoloration-preventing agent, filler, excipient, and binder. Further, The powder can be arbitrarily used intact or, if necessary, after mixing with fillers, excipients, binders, etc., and them formed into products with different shapes such as granules, spheres, sticks, plates, cubes, tablets, etc.

EXAMPLE A-4-a

Preparation of Aqueous Maltose Solution

A suspension, containing one part by weight of corn starch and two parts by weight of water, was admixed with "SPITASE HS", a bacterial liquefying α-amylase commercialized by Nagase & Co., Ltd., Osaka, Japan, and gelatinized by heating at 90° C. The resulting liquefied starch solution having a DE of 4.3 was obtained by heating the gelatinized solution immediately to 130° C. to stop the enzyme reaction. The liquefied starch solution was cooled to 55° C. rapidly, admixed with 50 units/g-starch of a starch-debranching enzyme, isoamylase prepared by culturing a bacterium of the genus *Pseudomonas*, which is commercialized by Hayashibara Biochemical Laboratories Inc., Okayama, Japan, and 10 units/g-starch of "#1500", β-amylase from soybean commercialized by Nagase & Co, Ltd., Osaka, Japan, and saccharified for 40 hours with keeping the pH at 5.0. A saccharified solution having a maltose content of 74.1%, d.s.b., was obtained. The saccharified solution was purified in a usual manner by decoloration using activated charcoal and desalting using an ion-exchanger resin, and then concentrated under reduced pressure to obtain a solution comprising maltose, having a sugar concentration of 45%, as a material for chromatographic separation.

"AMBERLITE XT-1007 ($Na^+$-form, crosslinking degree 6%)", an alkaline-metal strong acid cation-exchanger resin commercialized by Japan Organo Co., Ltd., Tokyo, Japan, was used as a resin for chromatographic separation. The resin was packed into two jacketed-stainless steel columns having a diameter of 5.4 cm, which were then cascaded in series to give a total gel bed depth of 10 m.

Under the conditions of keeping the inner column temperature at 55° C., the saccharide solution as material was fed to the columns in a volume of 5% (v/v) and fractionated by feeding to the columns hot water heated to 55° C. at an SV (space velocity) of 0.3 to separate and eliminate high maltotriose content fractions, and then collected the high maltose content fractions comprising maltose in high content and other oligosaccharides. Subsequently, the saccharified solution was purified in a usual manner by decoloration using activated charcoal and desalting using an ion-exchanger resin, and then concentrated under reduced pressure to obtain a maltose solution. Sugar composition of the maltose solution was 9.8% of glucose, 87.4% of maltose, 1.0% of maltotriose, and 1.8% of maltotetraose or more.

EXAMPLE A-4-b

Preparation of Powdery Product Comprising HCBM

An aqueous solution comprising maltose, obtained in Example A-4-a, was concentrated to give a moisture content of 20%, transferred to a crystallizer, and admixed with 1% of HCBM as a seed crystal. The massecuite was gradually cooled under gentle stirring conditions to 32° C., and HCBM was partially crystallized over about 16 hours. The percentage of the crystal was 39%. Since the massecuite obtained from above crystallization has a relatively high viscosity, the viscosity was decreased to about 45,000 cp by heating without decreasing the percentage of the crystal when the massecuite was run using a high-pressure pump, and the massecuite was sprayed in a spray-dryer using a pressurized nozzle. The conditions for drying were set as below: the temperature of the hot air for drying was set to 90° C.; the blow mode was set to vertical, descendent, and parallel blow in the spray-dryer; and the flow was set to give the moisture of 9.5% of the dried powder taken out from the spray-dryer.

The resulting powder was immediately allowed to contact with 0.2% of anhydrous crystalline α-maltose by mixing, and kept at 90° C. and relative humidity (RH) of 20% for three hours. Subsequently, the powder was kept at 30° C. and RH 80% for five hours for aging, and a powdery product comprising HCBM having the crystallinity of 64.6% and moisture of 6.8% was obtained in a yield of 80%, d.s.b., to the material corn starch. The powder comprised 87.4%, d.s.b., of maltose, 9.8% of glucose, 1.0% of maltotriose, and 1.8% of saccharides with a glucose polymerization degree of four or higher, and comprised 12.7% of α-anomeric maltose as an isomer of maltose, and has a satisfactory solubility to aqueous solvents. The powder has an insubstantial hygroscopicity under the preservation conditions at 25° C. and RH 75.2%, a satisfactory preservation stability, fluidity, and handleability. The powder comprised a powder constructed by cohesion of particles, and comprised 53% of powder with a diameter larger than 150 µm but 300 µm or less in a grading analysis.

Since the powder has a satisfactory solubility to aqueous solvents, it can be advantageously used by allowing to dissolve in pastes, semi-solids, and solids as well as water and liquids containing relatively large amount of water in various compositions such as food products, tobacco, cigarettes, feeds, pet foods, cosmetics, and pharmaceuticals as a sweetener, taste-improving agent, quality-improving agent, stabilizer, discoloration-preventing agent, filler, excipient, and binder. Further, The powder can be arbitrarily used intact or, if necessary, after mixing with fillers, excipients, binders, etc., and them formed into products with different shapes such as granules, spheres, sticks, plates, cubes, tablets, etc.

EXAMPLE B-1

Sweetener

A granulated sweetener was prepared by mixing to homogeneity 0.5 part by weight of a powdery product comprising HCBM, obtained by the method in Example A-1-b, with 0.5 part by weight of an anhydrous crystalline sorbitol, 0.01 part by weight of "αG-SWEET®", α-glycosyl-stevioside commercialized by Toyo Sugar Refining Co., Ltd., Tokyo, Japan, and 0.01 part by weight of "ASPARTAME®", L-aspartyl-L-phenylalaninemethylester commercialized by Ajinomoto Co., Ltd., Tokyo, Japan, and by applying a granulator. The sweetener had a relatively high sweetening power and quality; the sweetening power was about two-folds higher than sucrose, and it was substantially a low-caloric sweetener. The product had a high stability and showed no degradation of comprised sweeteners with a high sweetening power. The product can be suitably used as a low-caloric sweetener to sweeten low-calorific food products for fat person and diabetics who restrict their calorie intake, and can be also used to sweeten food products with lesser inducibility of dental caries because the sweetener less induces acids by dental caries-inducing microorganisms and less forms insoluble glucans.

EXAMPLE B-2

Hard Candy 50 parts by weight of sucrose and 50 parts by weight of a powdery product comprising HCBM, obtained by the method in Example A-2-b were dissolved in 100 parts by weight of water with heating. The solution was concentrated by heating under reduced pressure to give a moisture content of less than 2%, admixed with 0.6 part by weight of citric acid and appropriate amounts of lemon-flavor and coloring, and shaped in a usual manner to obtain the captioned product. The products are stable and high-quality hard candies with a satisfactory crisp, color, taste, and flavor, no crystallization of sucrose, low hygroscopicity, and no dripping.

EXAMPLE B-3

Chewing Gum

Three parts by weight of gum base was melted by heating to give a soft texture, admixed with two parts by weight of "MABIT®", anhydrous crystalline maltitol commercialized by Hyashibara Shoji, Inc., Okayama, Japan, two parts by weight of xylitol, two parts by weight of a powdery product comprising HCBM, obtained by the method in Example A-3-b, one part by weight of "TREHA®", hydrous crystalline trehalose commercialized by Hayashibara Shoji, Inc., Okayama, Japan, and appropriate amounts of flavor and coloring, knead using a roll machine in a usual manner, shaped, and packed to obtain the captioned product. The product has a satisfactory texture, taste, and flavor, and is suitable as a chewing gum with a low cariogenicity and low calorie.

EXAMPLE B-4

Sweetened Condense Milk

Two parts by weight of a powdery product comprising HCBM, obtained by the method in Example A-4-b, and two parts by weight of sucrose were dissolved in 100 parts by weight of fresh milk, and sterilized by heating using a plate-heater. Subsequently, the milk was condensed to a concentration of 70%, and canned under sterile condition to obtain the captioned product. The product had a mild sweetness and a good taste, and can be advantageously used as a flavoring for fruits, coffee, cocoa, tea, etc.

EXAMPLE B-5

Beverage Containing a Lactic Acid Bacterium 175 parts by weight of skimmed dry milk, 60 parts by weight of a powdery product comprising HCBM, obtained by the method in Example A-4-b, and 50 parts by weight of "Nyuka-OLIGO®", a powdery product comprising lactosucrose in high content, commercialized by Hayashibara Shoji, Inc., Okayama, Japan, were dissolved in 1,150 parts by weight of water, and sterilized at 60° C. for 30 min. After cooling down to 40° C., 30 parts by weight of a starter containing lactic acid bacterium was inoculated into the solution according to the conventional method, and then cultured at 37° C. for 8 hours to obtain the captioned product. The product had a good taste and comprised oligosaccharides, and can be suitably used as a beverage containing a lactic acid bacterium, having activities of promoting *Bifidobacterium* growth and improving intestinal disorders as well as keeping the lactic acid bacterium stably.

EXAMPLE B-6

Powdery Juice 33 parts by weight of powdery orange juice, produced by spray drying, 50 parts by weight of a powdery product comprising HCBM, obtained by the method in Example A-4-b, 10 parts by weight of "MABIT®", anhydrous crystalline maltitol commercialized by Hayashibara Shoji, Inc., Okayama, Japan, 0.65 part by weight of anhydrous citric acid, 0.1 part by weight of malic acid, 0.2 part by weight of powdery crystalline L-ascorbic acid 2-glucoside commercialized by Hayashibara Shoji, Inc., Okayama, Japan, 0.1 part by weight of sodium citrate, 0.5 part by weight of "PF-20", pullulan commercialized Hayashibara Shoji, Inc., Okayama, Japan, and appropriate amounts of flavor and coloring were mixed to homogeneity and pulverized to fine powder. The resulting powder was put into a fluidized granulator, and the exhaust temperature was set to 40° C. Then, the powder was sprayed appropriate volume of 70% aqueous solution dissolved a powdery product comprising HCBM, obtained by the method in Example A-4-b, as a binder. After granulating for 30 minutes, resulting granule was measured and packed to obtain the captioned product. The product is a powdery juice having a juice content of about 30%, and is valuable as a high-quality juice which has no bad taste and smell.

EXAMPLE B-7

Beverage Containing Coffee 860 parts by weight of coffee extract was obtained by the steps of milling 100 parts by weight of roasted coffee beans, adding 1,000 parts by weight of hot water, and extracting. 450 parts by weight of the extract was mixed with 90 parts by weight of a powdery product comprising HCBM, obtained by the method in Example A-1-b, and 400 parts by weight of water containing appropriate amount of sodium bicarbonate to homogeneity to prepare a beverage containing coffee with a neutral pH. Cans were filled with the beverage in a usual manner, and sterilized by heating at 120° C. for 30 minutes to produce canned beverage containing coffee. The product is a high-quality beverage containing coffee with a satisfactory aroma and taste. The product kept the satisfactory taste after preserving at 60° C. for one month in a vending machine. The product is a high-quality beverage containing coffee keeping a satisfactory aroma and taste when preserved by cooling for summer season.

EXAMPLE B-8

Custard Cream 100 parts by weight of corn starch, 50 parts by weight of a powdery product comprising HCBM, obtained by the method in Example A-2-b, 60 parts by weight of "TREHA®", hydrous crystalline trehalose commercialized by Hayashibara Shoji, Inc., Okayama, Japan, 40 parts by weight of sucrose, and one part by weight of sodium chloride were adequately mixed, then admixed with 280 parts by weight of egg, and stirred. 1,000 parts by weight of boiled milk was gradually added to the solution, and then put on the fire and continued stirring. The heating was stopped when the paste was changed into transparent as a whole by gelatinization of corn starch. The paste was cooled and admixed appropriate amount of vanilla essence. Then, the resulting paste was measured, filled, and packed to obtain the captioned product. The product is a high-quality custard cream having a smooth gloss and a satisfactory taste, of which starch is prevented retrogradation.

EXAMPLE B-9

"Uiro" (a Sweet Rice Jelly)

90 parts by weight of rice powder, 20 parts by weight of corn starch, 70 parts by weight of "MABIT®", anhydrous crystalline maltitol commercialized by Hayashibara Shoji, Inc., Okayama, Japan, 50 parts by weight of a powdery product comprising HCBM, obtained by the method in Example A-1-b, and four parts by weight of "PF-20", pullulan commercialized by Hayashibara Shoji, Inc., Okayama, Japan, were mixed to homogeneity to produce a premix for "uiro", a rice jelly. The premix and appropriate amounts of powdered green tea and water were kneaded, placed in a vessel, and steamed for 60 min to produce "Matcha-uiro", a rice jelly with powdered green tea. The product has a satisfactory gloss, mouthfeel, and taste. The product is also suitable as a low calorie "uiro", a rice jelly, having a good keeping quality, of which starch is prevented retrogradation.

EXAMPLE B-10

"Gyuhi" (a Starch Paste)

Four parts by weight of glutinous rice powder was dissolved in six parts by weight of water, run into a wood mold of which spread by wet dishcloth. After steaming at 100° C. for 20 minutes, the paste was admixed with two parts by weight of a powdery product comprising HCBM, obtained by the method in Example A-2-b, and two parts by weight of sucrose, kneaded adequately, and shaped to obtain the captioned product. The product has a satisfactory taste and of which gelatinized glutinous rice starch is prevented retrogradation. Therefore, the product is relishable for a long time.

EXAMPLE B-11

"An" (a Bean-jam)

In a usual manner, 10 parts by weight of small bean as material was admixed with water, and boiled to soak astringency, scum, and water-soluble impurities, and about 21 parts by weight of granulated small bean-jam was obtained. The resulting raw bean-jam was admixed with 14 parts by weight of sucrose, three parts by weight of a powdery product comprising HCBM, obtained by the method in Example A-1-b, and seven parts by weight of water, and boiled. After adding small amount of salad oil, the bean-jam was kneaded in order not to crash it to obtain about 35 parts by weight of a captioned bean-jam product. The product has a stability without discoloration and syneresis, a satisfactory feel on the tongue and taste, and is suitable as material for confectioneries such as "an-pan" (a bun with a bean-jam), "manju" (a bun with a bean-jam), "dango" (a rice paste with a bean-jam), "monaka" (a cake with a bean-jam), "hyouka" (frozen dessert), and etc.

EXAMPLE B-12

Bread 100 parts by weight of wheat flour, two parts by weight of a yeast, five parts by weight of sucrose, five parts by weight of a powdery product comprising HCBM, obtained by the method in Example A-1-b, and 0.1 parts by weight of yeast food were kneaded with water, and the mixture was fermented at 26° C. for two hours, further aged for 30 minutes, and baked in a usual manner. The product is high-quality bread with a satisfactory color and internal texture, adequate elasticity, and mild sweetness.

EXAMPLE B-13

Bread 100 parts by weight of "JOHYO-KO AO", a rice powder commercialized by loki Nutrie Co., Ltd., Hyogo, Japan, 18 parts by weight of "GLURICH A", a gluten commercialized by Chiba-Seifun Co. Ltd., Chiba, Japan, three parts by weight of sucrose, four parts by weight of "TREHA®", hydrous crystalline trehalose commercialized by Hayashibara Shoji, Inc., Okayama, Japan, eight parts by weight of a powdery product comprising HCBM, obtained by the method in Example A-2-b, two parts by weight of sodium chloride, 2.5 parts by weight of "KAIYOU-KOHBO", yeast commercialized by Sankyo-Foods Co. Ltd., Ishikawa, Japan, 10 parts by weight of fresh cream, five parts by weight of non-sweetened condensed milk, four parts by weight of shortening, and 85 parts by weight of water were mixed using a mixer, and kneaded at 23° C. for six minutes with low speed and for three minutes with middle speed. After stopping for a while, the mixture was further kneaded for four minutes to produce a dough. Subsequently, the dough was fermented for 50 minutes as floor time. Then, the dough was divided, rounded, and shaped. After keeping for 20 minutes as bench time, the dough was further fermented at 40° C. for 50 minutes in a case with humidity of 80%. After the fermentation, the dough was baked for 45 minutes using a oven with upper temperature of 230° C. and lower temperature of 200° C. to produce a rice bread. The product is a bread with a satisfactory bulge, color, sectional texture, and taste, having a large increase of volume. The product shows no change of mouth feel after keeping in a refrigerator at 4° C. for one week, and has a good preservability without dryness by retrogradation.

EXAMPLE B-14

Icing 10 parts by weight of a powdery product comprising HCBM, obtained by the method in Example A-2-b and 1.2 parts by weight of a emulsifier (sugar ester) were mixed with heating, then admixed with 107 parts by weight of "TREHA®", hydrous crystalline trehalose commercialized by Hayashibara Shoji, Inc., Okayama, Japan, and admixed with 7.5 parts by weight of fat with keeping temperature at 45° C. to produce a icing. The product is an icing comprising refined crystalline trehalose, and having a satisfactory shapeability without stickiness and deterioration per day.

EXAMPLE B-15

Bonbon

Three parts by weight of a powdery product comprising HCBM, obtained by the method in Example A-3-b, 300 parts by weight of "TREHA®", hydrous crystalline trehalose commercialized by Hayashibara Shoji, Inc., Okayama, Japan, and 115 parts by weight of water were mixed and boiled down to give sugar concentration of Brix scale 70. The syrup was cooled down to 80° C., admixed with 40 parts by weight of brandy, and shaped in a usual manner to obtain the captioned product. The product is a high-quality bonbon comprising refined crystalline trehalose, and having a satisfactory brandy-flavor without deterioration per day.

EXAMPLE B-16

Ham 1,000 parts by weight of pork ham was uniformly rubbed with 15 parts by weight of sodium chloride and three parts by weight of potassium nitrate, and stacked in a refrigerated room for one day and one night. The ham was soaked in a salt solution consisting of 500 parts by weight of water, 100 parts by weight of sodium chloride, three parts by weight of potassium nitrate, 40 parts by weight of a powdery product comprising HCBM, obtained by the method in Example A-4-b, and spices, in a refrigerated room for seven days. Subsequently, in a usual manner, The salt pork ham was washed with cold water, bound with a string, smoked, cooked, cooled, and packed to obtain the captioned product. The product is a high-quality ham with a satisfactory color and taste.

EXAMPLE B-17

"Tsukudani" (a Food Boiled Down in Soy Sauce)

250 parts by weight of "kombu" (a kelp) which was cut squarely after removing sands and treating with acid was admixed with 212 parts by weight of a soy sauce, 318 parts by weight of amino acid solution, 35 parts by weight of a powdery product comprising HCBM, obtained by the method of Example A-3-b, and 20 parts by weight of sucrose, and stewed. The mixture was further admixed with 12 parts by weight of sodium glutamate and eight parts by weight of caramel sauce, and boiled to obtain "tsukudani" (a food boiled down in soy sauce) of "kombu" (a kelp). The product is "tsukudani" (a food boiled down in soy sauce) with a low cariogenicity. The color and gloss of the product is appetizing as well as its taste and flavor.

EXAMPLE B-18

Bath Agent

One part by weight of orange peel juice and 10 parts by weight of a powdery product comprising HCBM, obtained by the method in Example A-1-b were mixed to obtain a powdery product comprising orange peel extract. Five parts by weight of the powdery product, 90 parts by weight of "yakijio" (baked sodium chloride), two parts by weight of "TREHA®", hydrous crystalline trehalose commercialized by Hayashibara Shoji, Inc., Okayama, Japan, one part by weight of silicic anhydride, 0.5 part by weight of "αG-HESPERIDINE", α-glucosyl hesperidine commercialized by Hayashibara Shoji, Inc., Okayama, Japan, and two parts by weight of crystalline powder of L-ascorbic acid 2-glucoside commercialized by Hayashibara Shoji, Inc., Okayama, Japan, were mixed to produce a bath agent. The product is a high-quality bath agent with a rich orange flavor, which provides a skin of velvety texture and prevents chill after taking a bath, and can be used to dilute 100 to 10,000-fold with warm water for taking a bath.

EXAMPLE B-19

Cosmetic Cream

Two parts by weight of polyoxyethylenglycol monostearate, five parts by weight of self-emulsified glycerin monostearate, five parts by weight of a powdery product, obtained by the method in Example A-1-b, one part by weight of "αG-RUTIN®", α-glucosyl rutin commercialized by Hayashibara Co., Ltd., Okayama, Japan, one part by weight of crystalline powder of L-ascorbic acid 2-glucoside commercialized by Hayashibara Shoji, Inc., Okayarna, Japan, one part by weight of fluid paraffin, 10 parts by weight of glycerin trioctanoate, and appropriate amount of preservative were dissolved by heating in a usual manner, admixed with two parts by weight of L-lactic acid, five parts by weight of 1,3-butylene glycol, and 66 parts by weight of purified water, and emulsified using a homogenizer. The mixture was further admixed with appropriate amount of perfume, and stirred to produce a cosmetic cream. The product has an anti-oxidation activity and high stability, and can be advantageously used as a high-quality sunburn preventive, skin-care agent, whitening agent, etc.

EXAMPLE B-20

Tooth Paste 45 parts by weight of calcium phosphate (CaHPO4), 1.5 parts by weight of sodium lauryl sulfate, 25 parts by weight of glycerin, 0.5 part by weight of polyoxyethylenesorbitan laurate, 10 parts by weight of a powdery product comprising HCBM, obtained by the method in Example A-2-b, 0.02 part by weight of saccharin, 0.05 part by weight of a preservative, and 13 parts by weight of water were mixed to obtain the captioned product. The product is a tooth paste improved in unpleasant taste, having a satisfactory availability, without deteriorating the washing power of the detergent.

EXAMPLE B-21

Solid Preparation for Fluid Diet

A composition consisting of 100 parts by weight of a powdery product comprising HCBM, obtained by the method in Example A-3-b, 200 parts by weight of hydrous crystalline trehalose, 200 parts by weight of a powdery product comprising maltotetraose in high content, 270 parts by weight of powderized egg yolk, 209 parts by weight of skim milk, 4.4 parts by weight of sodium chloride, 1.8 parts by weight of potassium chloride, four parts by weight of magnesium sulfate, 0.01 part by weight of thiamine, 0.1 part by weight of sodium L-ascorbate, 0.6 part by weight of vitamin E acetate, and 0.04 part by weight of nicotinamide was prepared, filled 25 g each into dampproof laminate bags, and heat-sealed to obtain the captioned product. The product is a liquid diet with effective activity for intestinal disorder, which is sweetened by a powdery product comprising HCBM and hydrous crystalline trehalose. A bag of the product can be advantageously used for supplying energy to a living body by dissolving the contents into about 150 ml to about 300 ml of water to produce a liquid diet and by using orally or by tube feeding to nose, stomach, or intestines.

EXAMPLE B-22

Tablet 50 parts by weight of aspirin, 14 parts by weight of a powdery product comprising HCBM, obtained by the method in Example A-4-b, and four parts by weight of corn starch were mixed to homogeneity and then solidified using a machine to produce 680 mg/tablet of tablets with a thickness of 5.25 mm. The product, which prepared by using filling-ability of a powdery product comprising HCBM, has no hygroscopicity and a satisfactory physical strength and collapsability in water.

EXAMPLE B-23

Sugar-coated Tablet 150 mg of a raw tablet, used as core, was sugar-coated to give about 230 mg of sugar-coated tablet by using solution 1 consisting of 40 parts by weight of a powdery product comprising HCBM, obtained by the method in Example A-4-b, two parts by weight of "PF-20", pullulan commercialized by Hayashibara Shoji, Inc., Okayama, Japan, 30 parts by weight of water, 25 parts by weight of talc, and three parts by weight of titanic oxide. Subsequently, the resulting tablet was further sugar-coated by using solution 2 consisting of 65 parts by weight of a powdery product comprising HCBM, one part by weight of "PF-20", and 34 parts by weight of water. Furthermore, the resulting sugar-coated tablet was polished using wax to produce a sugar coated tablet having a satisfactory gloss and appearance. The product has a superior shock tolerance and keeps the high quality for a long time.

INDUSTRIAL APPLICABILITY

As is evident from the above, a powdery product comprising HCBM, powderized by a spray method, which comprises 86% (w/w) or more but less than 93% (w/w) of maltose and 2% (w/w) or more of glucose on a dry solid basis, and has a crystallinity of 62% or more but less than 72% of the present invention is a powder which comprises 7% (w/w) or more but less than 14% (w/w) α-anomeric maltose as an isomer of maltose, having a high-solubility in aqueous solvents and a satisfactory preservation stability, fluidity, and handleability. Although the powdery product comprising HCBM comprises saccharides other than maltose such as glucose, maltotriose, and oligosaccharides with a glucose polymerization degree of four or higher in a relatively high amount, 7% or more but less than 14%, it can be easily produced by spray method. Also, since the powdery product can be produced continuously in a relatively short period of time in a relatively high yield, the cost for the production is easily decreased.

According to the present invention, a powdery product comprising HCBM, having a high-solubility in aqueous solvents is easily produced in a relatively low-cost. The present invention is advantageous for not only starchy sugar manufactures but also users because it can be expected to improve the operation efficiency. Therefore, the establishment of the present invention would, therefore, greatly influence on the industrial fields such as food products, cosmetics, and pharmaceuticals.

What is claimed is:

1. A powder comprising crystalline β-maltose monohydrate, powderized by a spray method in such a manner of spraying a maltose solution obtainable by saccharifying a liquefied starch with α-amylase, β-amylase and starch-debranching enzyme, said powder comprising 86% (w/w) or more but less than 93% (w/w) of maltose, 2% (w/w) or more of glucose, and less than 2% (w/w) of maltotriose, on a dry solid basis; having 7% (w/w) or more but less than 14% (w/w) of α-anomeric maltose as an isomer of maltose; having a crystallinity of 62% or more but less than 72%.

2. A powder comprising crystalline β-maltose monohydrate, said powder being powderized by a spray method in such a manner of spraying a maltose solution obtainable by saccharifying a liquefied starch with α-amylase, β-amylase and starch-debranching enzyme, said powder comprising 86% (w/w) or more but less than 93% (w/w) of maltose, 2% (w/w) or more of glucose, and less than 2% (w/w) of maltotriose, on a dry solid basis; having 7% (w/w) or more but less than 14% (w/w) of α-anomeric maltose as an isomer of maltose; and having a crystallinity of 62% or more but less than 72%; wherein 60% (w/w) or more of said maltose powder has a particle size with a diameter larger than 106 μm, preferably, 40% (w/w) or more of said maltose powder has a particle size with a diameter larger than 150 μm but 300 μm or smaller.

3. A process for producing a powder comprising crystalline β-maltose monohydrate, said process comprising the steps of:
   (a) contacting a liquefied starch with α-amylase, β-amylase and starch-debranching enzyme to produce a maltose solution comprising 86% (w/w) or more but less than 93% (w/w) of maltose and 2% (w/w) or more of glucose, on a dry solid basis;
   (b) concentrating the resulting maltose solution;
   (c) crystallizing the resulting concentrate; and
   (d) powdering the resuting mixture by a spraying method to obtain said powder,
   wherein said powder comprises 86% (w/w) or more but less than 93% (w/w) of maltose and 2% (w/w) or more of glucose, and less than 2% (w/w) of maltotriose, on a dry solid basis; has 7% (w/w) or more but less than 14% (w/w) of α-anomeric maltose as an isomer of maltose; and has a crystallinity of 62% or more but less than 72%.

4. The process of claim 3, wherein said maltose solution to be powderized by said spraying method is in a massecuite form.

5. A powder comprising crystalline β-maltose monohydrate, said powder formed by spraying a maltose solution, said powder comprising 86% (w/w) or more but less than 93% (W/w) of maltose and 2% (w/w) or more of glucose, on a dry solid basis; having 7% (w/w) or more but less than 14% (w/w) of α-anomeric maltose as an isomer of maltose.

6. The powder according to claim 1 having satisfactory solubility in water.

7. The powder according to claim 2 having satisfactory solubility in water.

8. The powder according to claim 5 having satisfactory solubility in water.

* * * * *